United States Patent [19]

Pagani

[11] Patent Number: 5,750,080
[45] Date of Patent: May 12, 1998

[54] METHOD FOR IN-SITU MODERNIZATION OF A UREA SYNTHESIS REACTOR

[75] Inventor: Giorgio Pagani, Milan, Italy

[73] Assignee: Urea Casale S.A., Lugano-Besso, Switzerland

[21] Appl. No.: 793,995

[22] PCT Filed: Aug. 31, 1995

[86] PCT No.: PCT/IB95/00720

§ 371 Date: Mar. 7, 1997

§ 102(e) Date: Mar. 7, 1997

[87] PCT Pub. No.: WO96/07474

PCT Pub. Date: Mar. 14, 1996

[30] Foreign Application Priority Data

Sep. 9, 1994 [CH] Switzerland .................. 2751/94-2

[51] Int. Cl.$^6$ ............................................. B01J 8/04
[52] U.S. Cl. ............................................. 422/193
[58] Field of Search ............................................. 422/193

[56] References Cited

U.S. PATENT DOCUMENTS 5,304,353  4/1994  Dente et al. .................. 422/193

FOREIGN PATENT DOCUMENTS 2840885  4/1980  Germany .
1137853  12/1968  United Kingdom .

*Primary Examiner*—Edward J. Cain
*Attorney, Agent, or Firm*—Sughrue, Mion, Zinn, Macpeak & Seas, PLLC

[57] ABSTRACT

A method for in-situ modernization of a reactor for urea synthesis at high pressure and temperature of the type wherein a co-current flow of a gaseous phase and a liquid phase takes place, comprising a vertical tubular shell (2) in which is supported a plurality of horizontal perforated plates (6a–6f), calls for the step of providing on at least one of the perforated plates (6a–6f) a plurality of structurally independent caps (8) having at the top a plurality of holes (11) and forming with the plate a plurality of lateral apertures (13). Advantageously, the holes (11) and the apertures (13) define respective preferential paths of the gaseous phase and the liquid phase respectively, to achieve intimate mixing thereof.

18 Claims, 4 Drawing Sheets

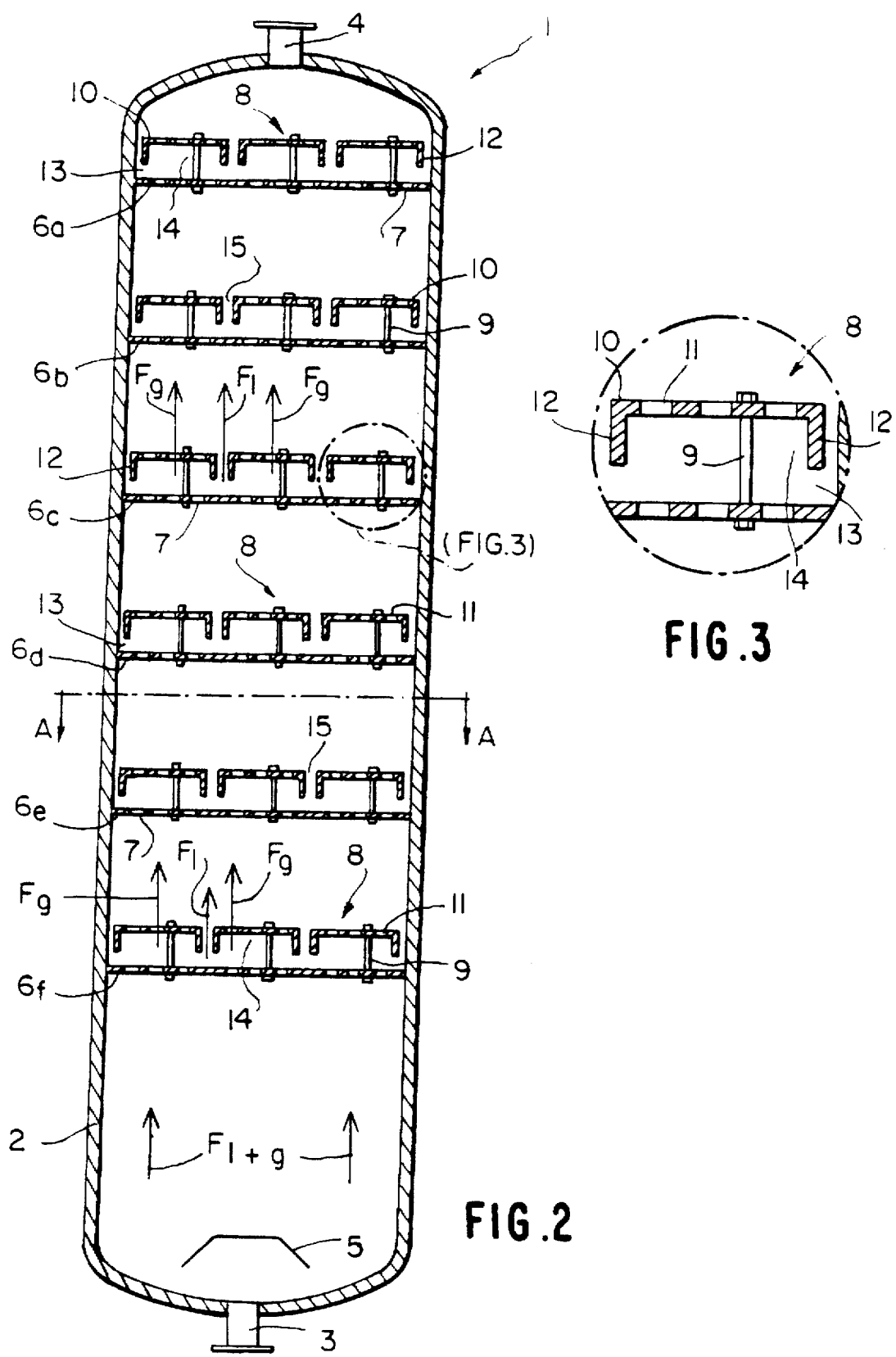

METHOD FOR IN-SITU MODERNIZATION OF A UREA SYNTHESIS REACTOR

FIELD OF APPLICATION

In a general aspect, the present invention relates to a method for in-situ modernization of reactors for the urea synthesis at high pressure and temperature.

The present invention also relates to a reactor for the urea synthesis at high pressure and temperature particularly but not exclusively achievable by means of the above said method.

In the description given below and in the following claims, the term "in-situ" modernization, is understood to mean the on-site modification of a pre-existing reactor in order to improve its performance and obtain e.g. greater production capacity and/or greater conversion yield and/or reduction in energy consumption.

In the terminology of the field this type of modernization is also termed "retrofitting" or "revamping".

In the field of urea synthesis at high pressure and temperature, the requirement for increasing the conversion yield of synthesis reactors to improve their Production capacity and reduce energy consumption in the urea plant is increasingly felt.

PRIOR ART

In order to satisfy said requirement, synthesis reactors comprising a vertical tubular shell in which is supported a plurality of superimposed horizontal perforated plates in mutually spaced relationship have been becoming increasingly used.

The urea is produced by intimate contact of a liquid phase and a gaseous phase comprising ammonia ($NH_3$) and carbon dioxide ($CO_2$) flowing co-currently in the reactor from below upward.

The perforated plates have the function of mixing together said phases to facilitate their intimate contact and hence exchange of mass and heat indispensable for conversion of the reagents, $NH_3$ and $CO_2$, into urea.

Synthesis reactors in accordance with the prior art are mainly of two types depending on the perforated plates used.

A first type of reactor comprises a plurality of superimposed perforated plates extending horizontally over the entire cross section of the reactor and in which is defined a plurality of holes for passage of a two-phase gas and liquid flow.

Since the liquid and gaseous phases pass through the same holes, there is alternating passage of gas and liquid with a pulsing flow which prevents intimate gas and liquid mixing. As a result there are low mass and heat transfer coefficients and hence low conversion yield.

A second type of reactor comprises a plurality of superimposed horizontal perforated plates in mutually spaced relationship. Between the peripheral edge of each of these plates and the internal wall of the reactor is defined an annular aperture.

Even in this case however it is not possible to obtain the desired intimate mixing between the liquid phase and the gaseous phase because the liquid flows preferably along said peripheral apertures while the gas tends to coalesce in the central part of the reactor.

Since they do not ensure effective intimate contact between the reagents the reactors in accordance with the prior art are not able to permit an optimal exchange of material and heat, which is the basic condition for achieving optimal conversion yield. Said reactors therefore operate far below their potential production capacity with resulting high energy consumption of the urea plant.

To overcome said drawbacks, U.S. Pat. No. 5,304,353 of this applicant describes a urea synthesis reactor capable of operating at high conversion yields thanks to the use of special perforated plates shaped in such a manner as to permit homogeneous mixing of the liquid and gaseous phases.

Replacement in the reactors according to the prior art described above of the original perforated plates by plates of new conception described in U.S. Pat. No. 5,304,353, although advantageous as regards conversion yield, necessitates a high investment cost not always economically justifiable.

SUMMARY OF THE INVENTION

The technical problem underlying the present invention is to increase conversion yield, improve the production capacity of synthesis reactors and reduce energy consumption in urea plants in accordance with the prior art mentioned above, while keeping the necessary investment costs to the minimum.

The above technical problem is solved according to the present invention by a method for in-situ modernization of a reactor for urea synthesis at high pressure and temperature of the type wherein a co-current flow of a gaseous phase and a liquid phase takes place, comprising a vertical tubular shell in which is supported a plurality of superimposed perforated plates extending horizontally in said shell, with said method characterized in that it comprises the step of providing on at least one of said perforated plates a plurality of structurally independent caps having at the top a plurality of holes, with said caps supported at a predetermined distance from said perforated plate with which they form a plurality of lateral apertures, said holes and said apertures defining respective preferential paths for the gaseous phase and the liquid phase respectively.

In the description given below and in the subsequent claims, the term "cap", is understood to mean an appropriately shaped and substantially concave covering element, in which is defined a chamber designed to receive a two-phase gas and liquid flow emerging from the plate.

It has been found that in the chamber takes place a separation of the two-phase flow. The gaseous phase tends to collect in the top of the chamber to then be distributed in a capillary manner, passing through the holes in the cap, in the liquid phase which, differently, emerges from the chamber through the apertures defined between the perforated plate and the cap.

The arrangement of appropriately perforated caps at a predetermined distance from the perforated plate permits, in addition, optimal separation of the gaseous and liquid phases. In fact, the latter traverse the cap along separate preferential paths defined by the holes and by the aforesaid apertures to then mix together in a continuous, homogeneous, finely distributed flow.

In this manner it is possible to achieve optimal mixing of the gaseous phase and the liquid phase flowing from the perforated plates. There is thus advantageously increased the intimate contact between reagents with resulting increase of the mass and heat transfer coefficients between liquid and gas.

Advantageously, the method according to the present invention allows achievement of an increase in conversion yield, improvement of the production capacity of the synthesis reactor and reduction of energy consumption of the urea plant, while using as far as possible the existing plates as support for the cap.

In order to obtain optimal redistribution of the gaseous phase in the liquid phase, the holes made in the cap have a diameter between 2 mm and 6 mm.

Indeed, it has been observed that holes having a diameter in the above mentioned range permit redistribution of the gaseous phase in the liquid phase in the form of small diameter bubbles which aid intimate contact of the two phases.

To permit a preferential flow of the liquid phase coming from the perforated plate and at the same time avoid the gaseous phase being entrained with the liquid phase, the lateral apertures have advantageously an opening between 50 mm and 150 mm.

In a preferred embodiment, the caps are substantially parallelepiped and have a cross section in the form of an overturned letter U. In addition they are advantageously provided on the perforated plate at a distance one from the other between 10 mm and 40 mm.

In this manner, it is possible to achieve optimal cover of the underlying perforated plate, with the formation of separate preferential paths for the liquid and gaseous phase permitting optimal separation of said phases, and at the same time ensuring a number of holes such as to allow optimal distribution of the gaseous phase in the liquid phase.

In accordance with an alternative form, the caps have a substantially trapezoidal cross section so as to aid conveyance of the gaseous phases towards the holes.

Advantageously, the caps have a thickness significantly less than that of the perforated plate to which they are fixed in a removable manner. This allows provision in said caps of small diameter holes by means of punching and hence low production costs.

In accordance with another aspect of the present invention there is also made available a reactor for urea synthesis at high pressure and temperature of the type wherein a co-current flow of a gaseous phase and a liquid phase takes place, comprising:

a vertical external shell of substantially cylindrical form, a plurality of superimposed perforated plates extending horizontally and in mutually spaced relationship in said shell for passage of a liquid phase and a gaseous phase, and characterized in that it also comprises on at least one of said perforated plates a plurality of structurally independent caps having at the top a plurality of holes, with said caps supported at a predetermined distance from said plate with which they form a plurality of lateral apertures, said caps and said apertures defining respective preferential paths for the gaseous phase and the liquid phase respectively.

The characteristics and advantages of the present invention are set forth in the description of an example of implementation of the modernization method according to the present invention, given below by way of non-limiting example with reference to the annexed drawings.

BRIEF DESCRIPTION OF THE DRAWINGS

In the drawings:

FIG. 2 shows a longitudinal cross section view of a reactor obtained by modifying the urea synthesis reactor of FIG. 1 by the modernization method according to the present invention;

FIG. 3 shows an enlarged scale cross section view of some details of the reactor of FIG. 2;

DETAILED DESCRIPTION OF A PREFERRED EMBODIMENT

Figure 1:
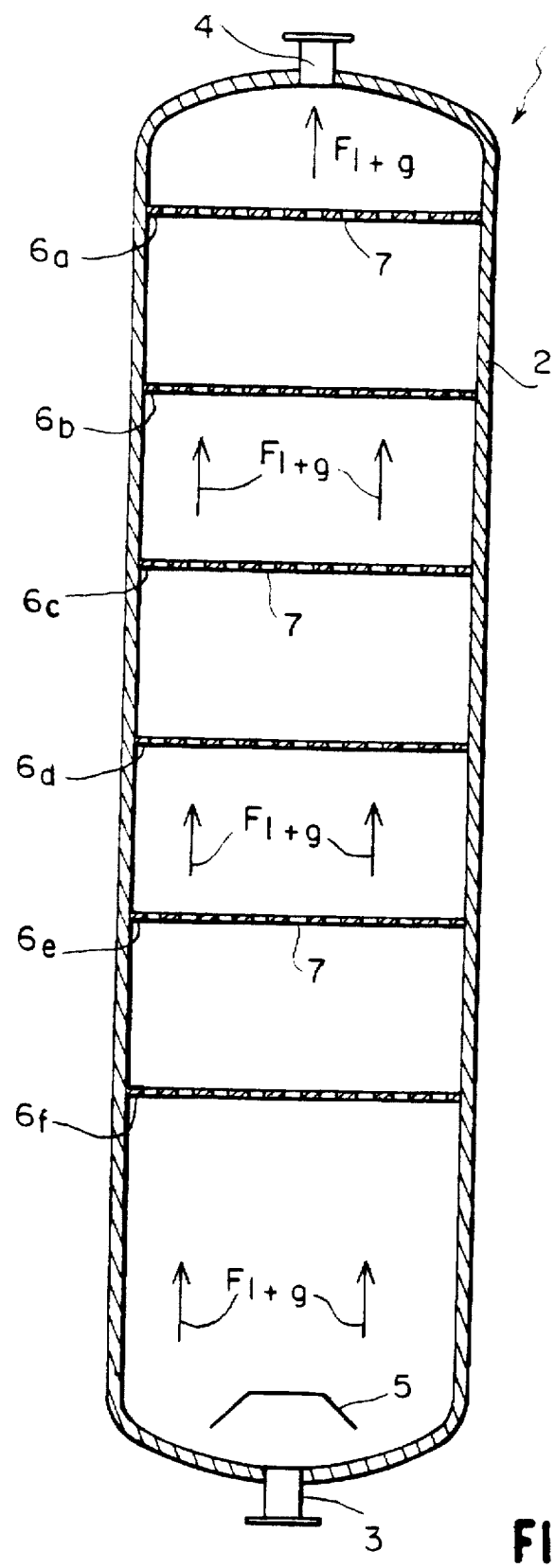
FIG. 1 shows a longitudinal cross section view of a reactor for urea synthesis at high pressure and temperature according to the prior art.

In the following description, the method in accordance with the present invention is described with reference to a reactor for urea synthesis at high pressure (100 bar–300 bar) and temperature (180° C.–220° C.) illustrated Said reactor is indicated by reference number 1 in the figure and comprises a vertical tubular shell 2 having at its ends apertures 3, 4 respectively for inlet of reagents including $NH_3$ and $CO_2$ and outlet of the reaction products. The reagents traverse the reactor 1 in the form of a liquid phase and a gaseous phase.

A deflector 5 is provided in the shell 2 near the aperture 3 to deflect the flow of reagents entering the reactor 1.

6a–6f indicate a plurality of superimposed horizontal perforated plates in mutually spaced relationship. The plates 6a–6f have respective pluralities of holes all indicated by 7 and of predetermined diameter, e.g. between 3 mm and 12 mm.

The perforated plates are distributed along the height of the reactor and have the function of distributing the gaseous phase in swarms of bubbles of small diameter to increase the material and heat exchange surface area between the ammonia and the $CO_2$.

In the reactor of FIG. 1, the perforated plates 6a–6f extend horizontally completely across the cross section of the shell 2.

In FIG. 1, the arrows Fl+g indicate the path of the reagents through the perforated plates 6a–6f. The flow of the gaseous phase and the liquid phase in the reactor 1 is substantially of the piston type, with pulsing motion due to the fact that liquid and gas traverse the holes 7 alternately.

In FIG. 2 is indicated as a whole a high pressure and temperature urea synthesis reactor obtained by modifying the reactor of FIG. 1 by the modernization method according to the present invention.

In said figure the details of the reactor 1 structurally and functionally equivalent to those shown in FIG. 1 are indicated by the same reference numbers and not further described.

In accordance with the method of the present invention the reactor 1 of FIG. 1 is modernized by providing on at least one of the perforated plates 6a–6f a plurality of caps 8 structurally independent, and fixed in a removable manner to the perforated plates 6a–6f by means of special spacers 9 supporting the caps 8 at a predetermined distance from the perforated plates 6a–6f. Known conventional fixing means such as e.g. bolts can be used for fixing the spacers 9 respectively to the caps 8 and to the perforated plates 6a–6f.

In the example of FIG. 2, the caps 8 have a substantially parallelepiped form and comprise an upper wall 10 having a plurality of holes, all indicated by 11, of predetermined diameter preferably between 2.5 mm and 2 mm, and four lateral walls 12 extending downward.

Advantageously the lateral walls 12 have a height preferably between 50 mm and 100 mm so as to promote the collection of the gaseous phase in the caps 8, to achieve optimal separation of the gaseous phase from the liquid phase.

Between the walls 12 of the caps 8 and the perforated plates 6a–6f are defined respective lateral apertures 13 extending the entire length of the walls 12 and having an opening preferably between 60 mm and 130 mm.

A chamber 14 separating the gaseous phase from the liquid phase is thus formed between the caps 8 and the perforated plate 6a–6f, the holes 11 and the apertures 13 defining respective preferential paths for the gaseous phase and the liquid phase respectively, as indicated by the arrows Fg and Fl.

Figure 4:
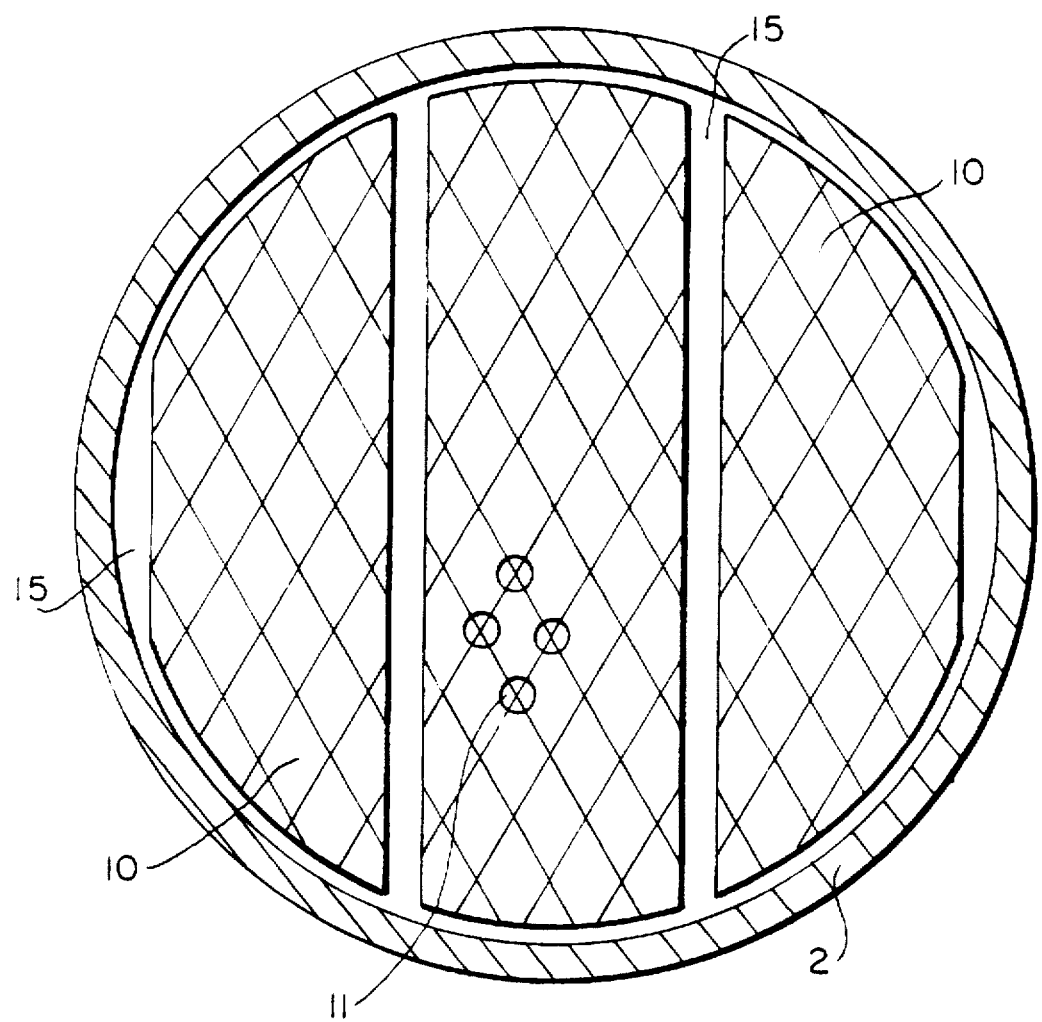
FIG. 4 shows an enlarged scale cross section view of the reactor of FIG. 2, along lines A—A of FIG. 2.

The special arrangement of the caps 8 on the perforated plates 6a–6f is better illustrated in FIG. 3, showing in enlarged scale some details of the reactor 1 of FIG. 2, and in FIG. 4, showing a cross section view of the reactor along lines A—A of FIG. 2.

Advantageously the caps 8 are provided on said at least one perforated plate 6a–6f in mutually spaced relationship so as to define a passage 15 for the liquid phase, generally between 15 mm and 25 mm wide.

In an alternative embodiment of the present invention the cap 8 can have other and different conformations among which that of a parallelepiped with trapezoid or triangular cross section, cylindrical or with spherical cap, and that of a parallelepiped with semicircular cross section.

In another embodiment (not shown), the caps 8 can be provided on said at least one perforated plate 6a–6f in direct contact therewith. In this special case the lateral apertures for passage of the liquid phase are made in the caps near the perforated plate.

Figure 5:
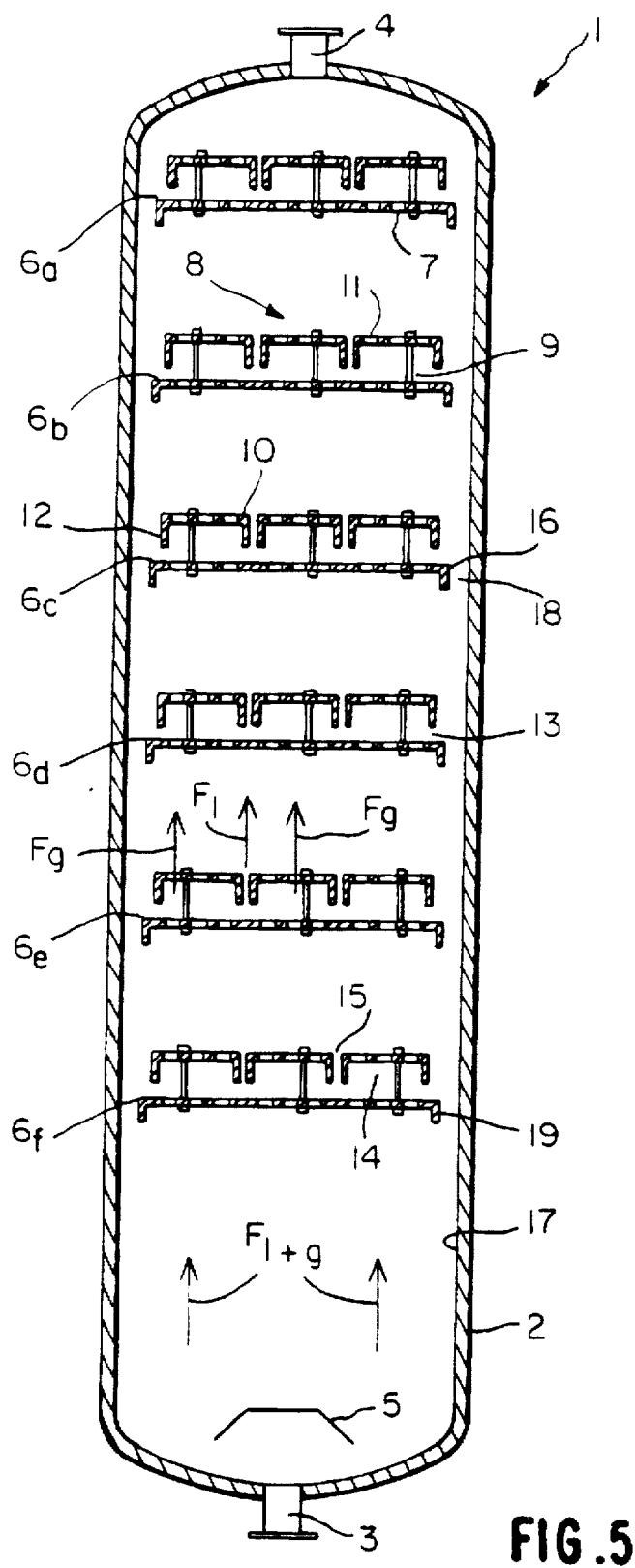
FIG. 5 shows a longitudinal cross section view of another reactor obtained by modifying a conventional reactor for urea synthesis at high pressure and temperature by the modernization method according to the present invention.

In FIG. 5 there is indicated as a whole another example of a reactor for the synthesis of urea at high pressure and temperature modernized by the method according to the present invention.

In said figure, the details of the reactor 1 structurally and functionally equivalent to those shown in FIGS. 1 and 2 are indicated by the same reference numbers and not further described.

In the example of FIG. 5, the perforated plates 6a–6f have a diameter smaller than the inside diameter of the shell 2, so as to define between a peripheral edge 16 of each plate 6a–6f and the inner wall 17 of the shell 2 an annular aperture 18.

The perforated plates 6a–6f of FIG. 5 are also provided with a collar 19 extending downward along the entire peripheral edge 16 of the plate.

In FIG. 5, the arrows Fl+g, Fg and Fl indicate the path in the reactor 1 of a two-phase flow, of the gaseous phase and of the liquid phase, respectively.

Operation of the urea synthesis reactor according to the present invention is as follows.

With reference to FIGS. 2 and 5, a two-phase flow of gas and liquid indicated by the arrow Fl+g is fed into the reactor 1 through the inlet aperture 3. The gaseous phase and the liquid phase flow in co-current in the shell 2 and traverse by piston flow the perforated plates 6a–6f while mixing together partially.

Upon outlet from said plates 6a–6f the two-phase flow is separated as indicated by the arrows Fl and Fg showing the preferential path respectively of the liquid phase and the gaseous phase.

Specifically, the liquid phase, once in the chamber 14 defined between the caps 8 and the perforated plate 6a–6f, is deviated with a continuous and homogeneous flow through the apertures 13 and the passage 15 to the next perforated plate. The gaseous phase collects in the top of said chamber 14 to then flow through the holes 11 and be redistributed in a capillary manner in a swarm of small bubbles in the liquid phase coming from the passage 15.

Differently from the pulsing flow characteristic of the perforated plates in accordance with the prior art, the flow of the gaseous phase into the liquid phase is continuous, homogeneous and finely distributed to promote optimal mixing of the phases.

In this manner it is possible to increase the intimate contact between the reagents and consequently obtaining an increase in conversion yield and production capacity of the modernized reactor while reducing energy consumption.

In the example set forth below there are compared by way of merely indicative and non-limiting example the conversion yields achievable by a reactor modernized by the method of the present invention and by a reactor according to the prior art.

EXAMPLE 1

The conversion yield achievable by a reactor modernized by the method of the present invention was compared with that achievable by a conventional reactor as shown in FIG. 1.

The two reactors considered have the following dimensions:

Inside diameter of shell: 2.3 m

Useful height: 35.0 m

The operating conditions are the following:

Pressure: 152 ata

Temperature: 190° C.

Molar ratio, $NH_3/CO_2$: 3.6

$H_2O/CO_2$: 0.7

The conventional reactor contains 10 perforated plates distributed along the useful height of the reactor and extending horizontally for the entire cross section of the shell.

In the modernized reactor, on the perforated plates were provided 5 parallelepiped caps with rectangular cross section spaced 20 mm one from the other, so as to achieve a structure like that shown in FIG. 2 and FIG. 4. The caps comprise an upper wall having a plurality of 3 mm holes and opposing lateral walls extending downward having a height of 70 mm. The caps are appropriately spaced from the perforated plate so as to form respective lateral apertures of 60 mm.

By means of a consolidated kinetic model described in the publication "Gas-Liquid Reactor in the Synthesis of Urea", M. Dente et al., Chemical Reactor Engineering, Vol. 47, no. 9/11, Jun. 8, 1992, the conversion yield was then determined (in terms of molar %) of the $CO_2$ in urea coming out the reactor.

The conversion yield is set forth below:

Conventional reactor: 60.0%

Modernized reactor: 63.0%

An increase in yield of 3.0 percentage points in the reactor according to the present invention is a very considerable result in the urea synthesis field, because it permits reduction of the recycling of the unreacted products to the reactor by 7–10% with a resulting significant increase in the production capacity of the synthesis reactor and a reduction in energy consumption of the urea plant.

From the foregoing description there emerge clearly the numerous advantages achieved by the present invention, and among which are an increase in the conversion yield, improvement in the production capacity in the synthesis reactors and reduction in energy consumption of the urea plants, with low investment costs thanks to the use of the existing plates as support for the caps.

Obviously, these advantages are achievable by modernizing a reactor of known type or providing an entirely new urea synthesis reactor.

I claim:

1. Method for in-situ modernization of a reactor for urea synthesis at high pressure and temperature, of the type wherein a co-current flow of a gaseous phase and a liquid phase takes place, comprising a vertical tubular shell (2) in which is supported a plurality of superimposed Perforated plates (6a–6f) extending horizontally in said shell (2), with said method characterized in that it comprises the step of providing on at least one of said perforated plates (6a–6f) a plurality of structurally independent caps (8) having at the top a plurality of holes (11), with said caps (8) supported at a predetermined distance from said perforated plate (6a–6f) with which they form a plurality of lateral apertures (13), said holes (11) and said apertures (13) defining respective preferential paths for the gaseous phase and the liquid phase respectively.

2. Method according to claim 1, characterized in that said caps (8) are substantially parallelepiped.

3. Method according to claim 2, characterized in that said caps (8) have a substantially trapezoidal cross section.

4. Method according to claim 1, characterized in that said caps (8) are provided on said at least one plate (6a–6f) at a predetermined distance between 10 mm and 40 mm.

5. Method according to claim 1, characterized in that said caps (8) are supported by said plate (6a–6f).

6. Method according to claim 5, characterized in that said caps (8) are fixed in a removable manner to said plate (6a–6f).

7. Method according to claim 1, characterized in that said holes (11) have a diameter between 2 mm and 6 mm.

8. Method according to claim 1, characterized in that said apertures (13) have an opening between 50 mm and 150 mm.

9. Method according to claim 1, characterized in that said caps (8) comprise a plurality of lateral walls (12) extending downward, with a height between 50 mm and 100 mm.

10. Reactor for urea synthesis at high pressure and temperature of the type wherein a co-current flow of a gaseous phase and a liquid phase takes place, comprising:

a vertical external shell (2) of substantially cylindrical form, a plurality of superimposed perforated plates (6a–6f) extending horizontally and in mutually spaced relationship in said shell (2) for passage of a liquid phase and a gaseous phase, characterized in that it also comprises on at least one of said perforated plates (6a–6f) a plurality of structurally independent caps (8) having at the top a plurality of holes (11), with said caps (8) supported at a predetermined distance from said plate (6a–6f) with which they form a plurality of lateral apertures (13), said caps (8) and said apertures (13) defining respective preferential paths for the gaseous phase and the liquid phase respectively.

11. Reactor according to claim 10, characterized in that said caps (8) are substantially parallelepiped.

12. Reactor according to claim 11, characterized in that said caps (8) have a substantially trapezoidal cross section.

13. Reactor according to claim 10, characterized in that said caps (8) are provided on said at least one plate (6a–6f) in mutually spaced relationship.

14. Reactor according to claim 10, characterized in that said caps (8) are supported by said plate (6a–6f).

15. Reactor according to claim 14, characterized in that said caps (8) are fixed in a removable manner to said plate (6a–6f).

16. Reactor according to claim 10, characterized in that said holes (11) have a diameter between 2 mm and 6 mm.

17. Reactor according to claim 10, characterized in that said apertures (13) have an opening between 10 mm and 40 mm.

18. Reactor according to claim 10, characterized in that said caps (8) comprise a plurality of lateral walls (12) extending downward, with a height between 50 mm and 100 mm.

* * * * *